US012748109B2

(12) United States Patent
Pugia

(10) Patent No.: US 12,748,109 B2
(45) Date of Patent: Sep. 29, 2026

(54) MICROWELL MICROELECTRODE FILTRATION SENSOR

(71) Applicant: BioMEMS Diagnostics, Inc., Bloomfield Hills, MI (US)

(72) Inventor: Michael J. Pugia, Pagosa Springs, CO (US)

(73) Assignee: BioMEMS Diagnostics Inc., Bloomfield Hills, MI (US)

( * ) Notice: Subject to any disclaimer, the term of this patent is extended or adjusted under 35 U.S.C. 154(b) by 0 days.

(21) Appl. No.: 18/030,636

(22) PCT Filed: Oct. 8, 2021

(86) PCT No.: PCT/US2021/054237
§ 371 (c)(1),
(2) Date: Apr. 6, 2023

(87) PCT Pub. No.: WO2022/076861
PCT Pub. Date: Apr. 14, 2022

(65) Prior Publication Data

US 2023/0408507 A1 Dec. 21, 2023

Related U.S. Application Data

(60) Provisional application No. 63/089,328, filed on Oct. 8, 2020.

(51) Int. Cl.
*G01N 33/543* (2006.01)
*G01N 1/40* (2006.01)
(Continued)

(52) U.S. Cl.
CPC ....... *G01N 33/5438* (2013.01); *G01N 1/4005* (2013.01); *G01N 27/3276* (2013.01);
(Continued)

(58) Field of Classification Search
CPC ............. G01N 33/5438; G01N 1/4005; G01N 27/3276; G01N 27/44743;
(Continued)

(56) References Cited

U.S. PATENT DOCUMENTS

2013/0203620 A1* 8/2013 Glezer ................ B01L 3/50855 506/9
2016/0228819 A1 8/2016 Hansford et al.
(Continued)

FOREIGN PATENT DOCUMENTS

WO 2021206752 A1 10/2021

OTHER PUBLICATIONS

Wayment et al., "Biotin-Avidin Binding Kinetics Measured by Single-Molecule Imaging," 2009, Analytical Chemistry, vol. 81, pp. 336-342 (Year: 2009).*

(Continued)

*Primary Examiner* — Shizhi Qian
(74) *Attorney, Agent, or Firm* — The Webb Law Firm

(57) ABSTRACT

A microwell microelectrode filtration sensor created by using an inert planar surface, which can be a metal pattern dry etched, to generate a filtration membrane with pores, generating a reactive metal surface layer as a working electrode. The electrode is within an area covering a filtration membrane, and makes one or more microwells added by a first layer of inert plastic of an effective working distance height and a second layer of a non-reactive metal of an effective microwell surface area to serve counter and/or reference an electrode. This is followed by at least one layer of inert plastic or metal.

8 Claims, 5 Drawing Sheets

(51) Int. Cl.
*G01N 27/327* (2006.01)
*G01N 27/447* (2006.01)
*G01N 33/569* (2006.01)

(52) U.S. Cl.
CPC . *G01N 27/44743* (2013.01); *G01N 27/44791* (2013.01); *G01N 33/56911* (2013.01)

(58) Field of Classification Search
CPC ....... G01N 27/44791; G01N 33/56911; G01N 2001/4016; G01N 2001/4038
See application file for complete search history.

(56) References Cited

U.S. PATENT DOCUMENTS

| | | | |
|---|---|---|---|
| 2016/0291001 | A1 | 10/2016 | Revzin et al. |
| 2018/0095067 | A1* | 4/2018 | Huff ................. G01N 33/48721 |
| 2018/0283998 | A1 | 10/2018 | Pugia et al. |
| 2019/0290170 | A1* | 9/2019 | Chen ....................... C23C 18/30 |
| 2020/0072825 | A1 | 3/2020 | Hosseini et al. |
| 2020/0326325 | A1* | 10/2020 | Diamond .............. B01L 3/5027 |
| 2023/0158488 | A1 | 5/2023 | Pugia |

OTHER PUBLICATIONS

Valentine, "Wafer selection guide," 2020, inseto, pp. 1-5 (Year: 2020).*

Kafka et al., Micro-drilling of polymer tubular ultramicroelectrode arrays for electrochemical sensors, Sensors, 2013, 13, 6319-6333 (Year: 2013).*

Luo et al., "Application of Nanoparticles in Electrochemical Sensors and Biosensors", Electroanalysis, 2006, pp. 319-326, vol. 18:4.

Nguyen et al., "Immobilized Enzymes in Biosensor Applications", Materials, 2019, pp. 1-34, vol. 12:121.

Pugia et al., "Multiplexed Signal Ion Emission Reactive Release Amplification (SIERRA) Assay for the Culture-Free Detection of Gram-Negative and Gram-Positive Bacteria and Antimicrobial Resistance Genes", Anal Chem., May 2021, pp. 1-20, vol. 93:17.

Zhu et al., "Electrochemical Sensors and Biosensors Based on Nanomaterials and Nanostructures", Analytical Chemistry, 2015, pp. 230-249, vol. 87.

* cited by examiner

MICROWELL MICROELECTRODE FILTRATION SENSOR

CROSS REFERENCE TO RELATED APPLICATIONS

This application is the United States national phase of International Application No. PCT/US21/54237 filed Oct. 8, 2021, and claims priority to U.S. Provisional Patent Application No. 63/089,328, filed Oct. 8, 2020, the disclosures of which are hereby incorporated by reference in their entireties.

BACKGROUND OF THE INVENTION

Field of the Invention

The present disclosure relates to analyte detection microwells which include a size exclusion filter with one or more pores and electrochemical detector and allows biomolecule capture from complex samples under low hydrodynamic force, and enables electrochemical immunoassay detection of biomolecules. The present disclosure allows processing complex biological samples such as whole blood, serum, plasma, urine, wound fluid, bronchial lavage, and sputum specimens from 0.1 μL to 100 mL to allow capture and detection of cellular and cell free biomolecules.

Technologies capable of making analyte detection microwells which include a size exclusion filter with one or more pores and electrochemical detector are limited. Typically, issues arise in this field due to significant sensor failures and costly fabrication due to slow and complex manufacturing processes. Therefore, it is desirous to create an analyte detection microwell capable of rapid fabrication and low sensor failures to maximize sensitivity and minimize cost of analyte detection microwells used for biomolecule capture and detection.

Description of Related Art

IBRI's PCT/US2020/055931, which is incorporated by reference in its entirety, (the "IBRI PCT") has recently demonstrated a device format that could perform multiplexed analysis of biomolecules directly on complex samples using multiple analyte detection microwells for electrochemical detection of target analytes. The analyte detection microwell includes a size exclusion filter with one or more pores, electrochemical detector, and affinity agents for analyte capture and detection which operates under low hydrodynamic force. The affinity agent for detection is attached to a reagent capable of generating an electrochemical label. The affinity agent for capture is attached to a reagent capable of binding a surface in the microwell. The electrochemical label is detected by a working electrode and reference/counter electrode placed in the microwell to measure label formed by the affinity agent for detection. The format enables processing of biomolecule capture and immunoassay detection in a convenient format without user intervention and having to remove the filtration membrane.

The IBRI PCT design allows precise containment of the small volume of liquids into analyte detection microwell without loss of liquid, exposure to the environment or the need for extraction and delivery into an analyzer. A microfluidic capillary stop is placed underneath multiple microwells to hold liquid in the microwells for capture and detection of the analyte measured. The device operates after manual dilution and mixing of sample with liquids and affinity reagents, such as the antibodies needed for immunoassay. The liquid reagents allowed the diluted sample and reagents to be moved for capture and detection inside the analyte detection microwell. Elimination of the manual dilution and mixing of a sample with liquids and affinity reagents is needed to allow the device to avoid any user intervention. Avoiding user intervention is preferred for the design to be used in the home testing and point of care testing settings. Avoiding the need for additional liquids, valves, and liquid dispensers is highly desired for miniaturization and ease of use.

The IBRI PCT device can be used with reagents for affinity assay such as electrochemical immunoassay (EC-IA), optical immunoassay (OP-IA), and mass spectrometric immunoassays (MS-IA) in the detection of cells and biomolecules trapped on the filtration membrane. In one example, polyclonal affinity reagents were used as a sandwich assay pair by placing an affinity label (biotin) on some of the polyclonal antibodies and placing a detection method (ALP) on the remaining polyclonal antibodies. This format allows the biomolecules to be immediately captured on the filtration membrane using neutravidin attached to capture microparticles trapped on the membrane surface. For multiplexed analysis, the filtration membrane is divided into multiple micro-wells each with a filtration membrane bottom. Descriptions of the affinity assays utilized may be found in Pugia, M. J. et al., "Multiplexed SIERRA Assay for the Culture-Free Detection of Gram-Negative and Gram-Positive Bacteria and Antimicrobial Resistance Genes" Anal Chem, 2021.

The IBRI PCT format uses a capillary stop as a mechanism for stopping and re-starting the flow of liquids and samples through the device. The sample processing occurs by applying a hydrodynamic force in the waste collection chamber that pulls the sample and liquid reagent fluids through the sample capillary, and mixes the liquid in the sample well, and then moves the liquid through the filtration membrane with microwells. A vacuum or centrifuge force generates a hydrodynamic force in the waste collection chamber at a desired strength to pull the sample and liquid reagent into the waste collection chamber. The sample well is snapped into reaction well prior to use and removed after use for re-sealing the rest of the format in a biohazard bag to send off for confirmatory testing.

The principles of the IBRI PCT device to move and hold the sample and liquid reagents in analyte detection microwells with filtration membrane having one or more pores were demonstrated using a SiO2 microelectrode filtration membrane with microwells. The format includes a reaction well to hold the SiO2 microelectrode filtration membrane with microwells and a capillary stop below the SiO2 microelectrode filtration membrane. When a hydrodynamic force is applied in the waste collection chamber below the capillary stop, the hydrodynamic force pulls the sample and liquid reagent fluids through the reaction well, the SiO2 microelectrode filtration membrane, and the capillary stop. When hydrodynamic force is not applied, the capillary stop is capable of holding the sample and reacting fluids in the SiO2 microelectrode filtration membrane.

In practice, issues arise during microchip fabrication of SiO2 microelectrodes and micro filtration membranes. The result is significant failures preventing use, for example >1% of batch are lost. Additionally, microchip fabrication processing steps can be slow and small scale, which significantly increases the cost of the sensor and limits the amount produced. Microchip fabrication is based upon thermally grown dense SiO2, and these layers can only achieve up to a 20 micron thickness when making the micro filtration membrane with pore diameters greater than 10 microns. These thin filtration membrane frequently break after fabrication when the microwell size is greater than a 100 μm in diameter due to the fragility of the membrane. Additionally, placement of the microelectrodes on the bottom and top of the microwells requires additional processing steps. Process limitations restrict the separation distance and surface areas of the working electrode (WE), reference electrode (RE), and counter electrode (CE). Ideally the surface area of the working electrode (WE) should be maximized and should be twice the surface area of the combined counter and reference electrodes (CE/RE).

Another key issue is costly fabrication materials. For example, silica wafers at the highest scale possible have a larger material cost compared to plastics. Additionally, low-cost materials for electrodes, such as screen printed coatings, require a high temperature and cannot achieve thin monolayers that more expensive sputtered metals can achieve. Highly uniform coatings are needed for reproducible affinity reactions. Use of expensive machined metals or ceramic are also not cost effective.

Other fabrication methods for placement of electrodes require flat surfaces to allow highspeed printing for fabrication. Flat surface placement of electrodes does not maximize the size of working electrode as counter and reference electrodes must share the space. These electrodes must be separated by an effective working distance of at least half the working electrode size. If the working electrode or the reference electrode is 100 μm across, then these should be separated by at least a gap of 200 μm in most solutions. Additionally, screen printing is only reproducible to tolerances of 50 to 100 μm and printing small electrodes into microwells of hundreds of μm would be difficult to achieve. Lastly, screen printing onto a membrane with the μm size pore or slots of IBRI PCT device would clog the pore or slots thereof.

Therefore, it is desirous to find a solution whereby the membrane sensor may be rapidly fabricated and not be prone to failure, while maximizing sensor sensitivity and minimizing cost of the electrode. These sensors would allow high sensitivity and reliable detection of biomolecules and cells from complex fluids by electrochemical reactions; in particular, by holding and releasing the sample and/or liquids during incubating, mixing, and washing steps needed for affinity and separation protocols.

SUMMARY OF THE INVENTION

A non-limiting embodiment or example provides for one or more analyte detection microwells each with filtration membranes and microelectrodes by attaching at least 3 layers of planar surfaces. The bottom layer includes a filtration membrane with one or more pores and a reactive metal surface layer serving as a working electrode. The middle inert layer includes through holes creating microwells aligned with the filtration membrane in the bottom layer. The top layer includes through holes aligned with microwells and is a non-reactive metal serving as the counter and/or reference electrode. The thickness of the middle inert layer serves as an effective working distance height. Additional layers can be added and aligned with through holes for the analyte detection microwell and for connection to metal layers.

In non-limiting embodiments or examples, the detection microwells with a size exclusion filter having one or more pores and an electrochemical detector allows biomolecule capture from complex samples under low hydrodynamic force conditions and detection of biomolecules by detection of electrochemical labels. In other non-limiting embodiments, the affinity agent for capture is attached to metal capable of being a binding surface in the microwell. In other non-limiting embodiments or examples, the electrochemical label is detected by a working electrode comprised of a reactive metal surface layer and a non-reactive metal surface layer as a reference electrode and/or counter electrode.

Further non-limiting embodiments or examples are set forth in the following numbered clauses.

Clause 1: A device with working and counter/reference electrodes in a microwell made of metal and inert layers which have pores and/or microwell holes aligned in a stack of layers.

Clause 2: A device of clause 1 where at least one layer is of reactive metals, a second is of inert material, a third is of non-reactive metal.

Clause 3: A device of any of clauses 1-2 where at least one or more additional inert or metal layers is used.

Clause 4: A device of any of clauses 1-3, where at least one layer is of reactive metals as a working electrode is used for detection of electrochemical labels.

Clause 5: A device of any of clauses 1-4 where at least one layer is of non-reactive metals is a counter and/or reference electrode enabling detection of electrochemical labels.

Clause 6: A device of any of clauses 1-5 where the thickness of at least one inert layer is the working distance between the working and counter and/or reference electrodes enabling detection of electrochemical labels.

Clause 7: A device of any of clauses 1-6 where the thickness and diameter of the microwell holes is of inert material and non-reactive metal and defines volume of the microwell.

Clause 8: A device of any of clauses 1-7 where the thickness and diameter of the microwell holes is of reactive metal and defines volume of the working electrode.

Clause 9: A device of any of clauses 1-8 where affinity agents are attached to the reactive metal and not the inert material and non-reactive metal.

Clause 10: A method of using a microwell microelectrode filtration sensor, comprising: introducing an analyte to a microwell; introducing an affinity agent to the microwell; introducing a catalyst, thereby creating an electrochemical signal; and detecting the electrochemical signal.

Clause 11. The method of clause 10, further comprising introducing a second affinity agent to the microwell.

Clause 12. The method of any of clauses 10-11, further comprising capturing the analyte subsequent to detecting the electrochemical signal.

These and other features and characteristics of the present disclosure, as well as the methods of operation and functions of the related elements of structures and the combination of parts will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

BRIEF DESCRIPTION OF THE DRAWING(S)

DESCRIPTION OF THE INVENTION

Figure 1:
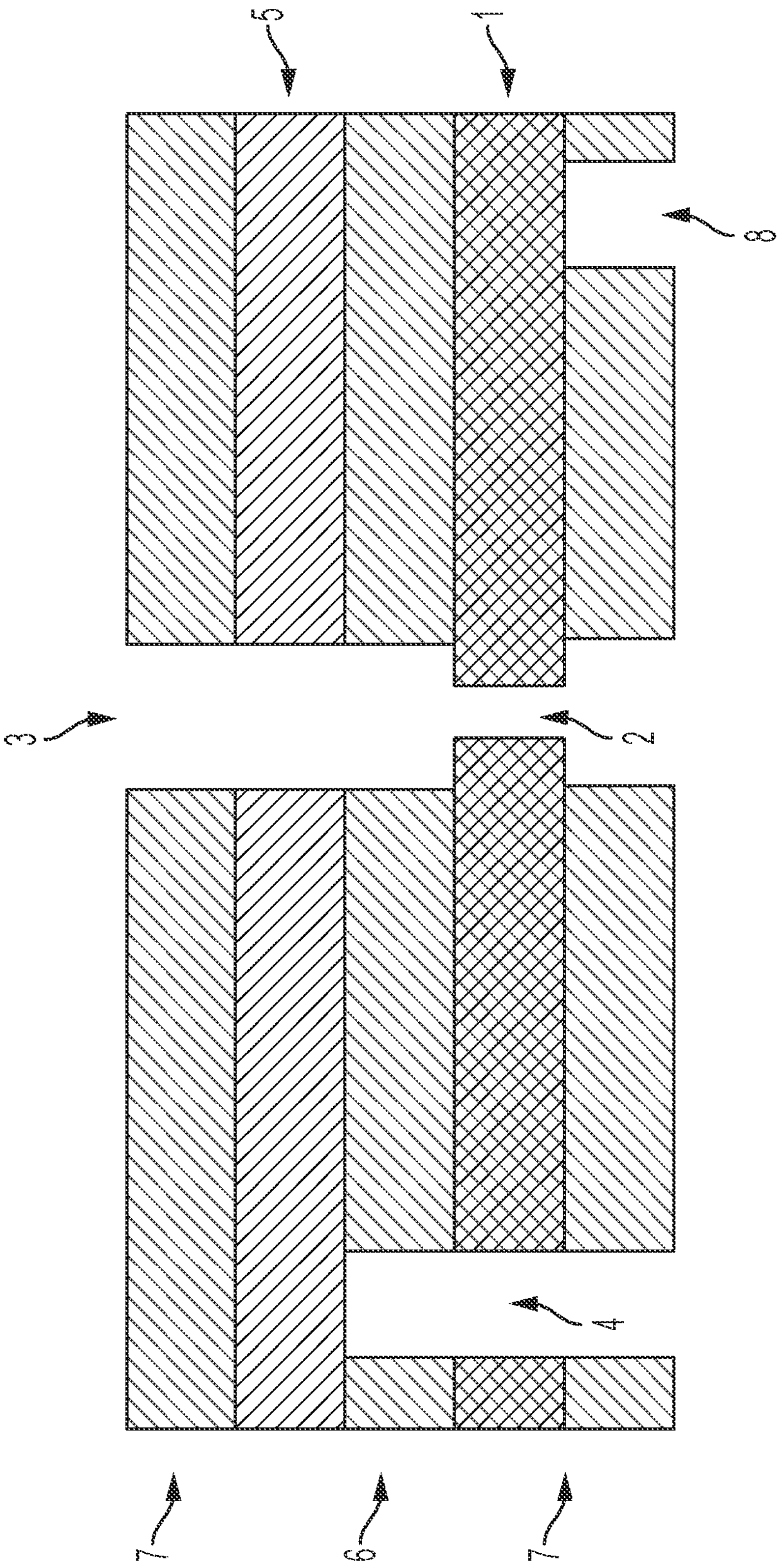
FIG. 1 shows a cross-sectional view of a non-limiting embodiment of a microwell microelectrode filtration sensor.

For the purpose of promoting an understanding of the principles of the invention, reference will now be made to the embodiments illustrated in the drawings, wherein like reference numbers correspond to like or functionally equivalent elements, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. Certain embodiments of the invention are shown in detail, but some features that are well known, or that are not relevant to the present invention, may not be shown for the sake of conciseness and clarity.

For purposes of the description hereinafter, the terms "end," "upper," "lower," "right," "left," "vertical," "horizontal," "top," "bottom," "lateral," "longitudinal," "forward," "reverse" and derivatives thereof shall relate to the example(s) as oriented in the drawing figures. However, it is to be understood that the example(s) may assume various alternative variations and step sequences, except where expressly specified to the contrary. It is also to be understood that the specific example(s) illustrated in the attached drawings, and described in the following specification, are simply exemplary examples or aspects of the invention. Hence, the specific examples or aspects disclosed herein are not to be construed as limiting. Moreover, as used in the specification and the claims, the singular form of terms, include plural referents unless the context clearly dictates otherwise.

For purposes of the description hereinafter, the material used for the analyte detection microwell can be created by alignment of through holes of one or more inert layers with through holes of metal layers. These through holes may be machined, milled, drilled, molded, or cast into the layers. For purposes of the description hereinafter, the material used for inert layers can be plastics or other non-porous materials such as ceramic, glass or metals. Examples of inert materials include alumina, ceramic, glass, alumina, polystyrene, polyalkylene, polycarbonate, polyolefins, epoxies, Teflon®, PET, cyclo olefin polymer (COP), cyclo olefin copolymer (COC) such as Topas®, chloro-fluoroethylenes, polyvinylidene fluoride, PE-TFE, PE-CTFE, liquid crystal polymers, Mylar®, polyester, polymethyl pentene, polyether ketone (PEEK), NEMA grade designation for glass-reinforced epoxy laminate material (FR4), polyimide (PI), polyphenylene sulfide, polydimethylsiloxane (PDMS), polyethylene terephthalate (PET), polyethylene naphthalate (PEN), polyimide (PI), polyurethane, poly(3,4-ethylenedioxythiophene) polystyrene sulfonate (PEDOT:PSS), polyacetylene, and polyaniline and PVC plastic films. These layers can be fabricated as multilayer, polymer ceramics, printed circuit board, and flexible circuit board. Adhesives, solder mask, solder stop mask and solder resist applied as a thin lacquer-like layer of polymers to the inert materials, non-reactive or reactive metal. Adhesives can used to adhere layers and construct multiple composite layers the inert materials, non-reactive or reactive metal with combine one or more materials. Adhesives can used to adhere Adhesives, solder mask, solder stop mask and solder can be used to protect layers and adhere layers. For purposes of the description hereinafter, the material used for reactive metal, can be gold, silver, palladium, and other metals reactive to forming a direct bond to thiols that can link to affinity agents such as 11-mercapotundecanoic acid. For purposes of the description hereinafter, the reactive metal can be coated as Electroless nickel immersion gold ENIG, Electroless Nickel Electroless Palladium Immersion Gold (ENEPIG) palladium and gold plating process (EPIG) and other plating. For purposes of the description hereinafter, the material used for non-reactive metal, can be metal, such as nickel, copper, zinc, and other metals not reactive to forming a direct bond to thiols. In some cases, these and other metals can be deactivated using blocking agents and thiols, such as 1-dodecane-thiol that cannot link to affinity agents. For purposes of the description hereinafter, the reactive and nonreactive metal layer can be connect to an analyzer to read the electrochemical signal generated through the reactive and non-reactive metal s by use of one or more traces and vias.

For purposes of the description hereinafter, the physical dimension used for the three planar surfaces that fabricate the analyte detection microwell can have varying layer thickness, for example of 5 to 5000 μm (1 mil is 25.4 μm) and number of microwells from 1 to 1000. Each microwell can have varying pore diameters, for example 50 to 1000 μm, varying pore numbers, for example 1 to 1000 pores per microwell, and varying microwell diameters and height, for example at least 50 μm to up to 1 cm In some non-limiting examples, there are eight 100 μm diameter pores with an area of 0.063 mm^2 per microwell. In some non-limiting examples, slots, e.g of 50×100 μm, are used as pores. In some non-limiting examples, there are four 200 micron diameter pores with an porosity of 0.128 mm^2 per microwell. In some non-limiting examples, microwell have diameters of 2000 μm and heights of 3000 μm with a bottom reactive metal area of 3.14 mm^2 per microwell and a microwell volume of 9.4 μL. In some non-limiting examples, 2% of the reactive metal surface area may have pores. In some non-limiting examples, 25% of the reactive metal surface area may have pores.

For purposes of the description hereinafter, the reactive metal surface is placed on an inert layer, by for example coating, depositing, and spraying. In some cases, the metal surface is a mono layer of metal. In some non-limiting examples, the physical dimension used for the surface layer serving as a working electrode covers the bottom of a microwell with a diameter of 2000 microns for metal area of 3.08 mm^2 per microwell when 0.06 mm^2 of the bottom of a microwell are used for pores. The non-reactive metal layer may have a thickness of 100 microns for cylindric counter/reference electrode with a surface area of 0.56 mm^2 on the inside of the microwell. In some non-limiting examples, the non-reactive metal layer is separated from the working electrode by an inert layer of 200 microns by height inside the microwell hole of 2000 microns in diameter for an effective working distance area of 1.25 mm^2 per microwell between the reactive and non-reactive metal layer. In some non-limiting examples, the bottom surfaces of the microwell are used for pores and the area reactive metal layer of is reduced to double the working distance area of 1.25 mm^2. In other non-limiting examples, the counter/reference electrode surface area is increased to at least half the size of working electrode area of 2.5 mm^2.

For purposes of the description hereinafter, the planar surfaces used for 2 layers of the metal surfaces produce reproducible electrical conductivities, resistances, surfaces, and mechanical properties. In some examples, the metal surfaces have reduced background resistance of <100 milli-ohms (mΩ) and are able to detect 0.05 to 3 microA cross the working and reference/counter electrodes at 0 to 3 V. In some examples, polymers, silicon or PTFE are deposited on the metal surfaces, and patterned to keep contact pads and microwells open and other areas electrically shielded. In other examples, the inert layers, of typical circuit board material such as FR4, are used to protect the metals and allow connections to the potentiostat using holes to connect to the microwell microelectrode.

In some non-limiting embodiment or example, the complete number of all WE in the microwell array are individually detected with 10 patterned or more connections, and 1 connection for a common counter and reference electrode (CE/RE electrode) as a 2-electrode system. In other non-limiting embodiment or example, the complete number of all WE and CE/RE in the microwell array are all individually detected with 10 patterned or more connections, and with 10 patterned or more common counter and reference electrode (CE/RE electrode). In other non-limiting embodiment or example, the CE and RE are separate layer and complete number of all WE, CE and RE in the microwell array are all individually detected with patterned or more connections allow as a 3-electrode system. In some cases more than one the CE and RE layer is allowed to provide multiple connection layers. FIG. 1 is a cross sectional schematic view of the construction of analyte detection microwell including a size exclusion filter and an electrochemical detector produced according to a non-limiting embodiment or example. FIG. 1 illustrates an embodiment of the present disclosure using 5 layers of planar surfaces. In this example, the reactive metal layer (1) includes a filtration membrane (2) having one or more pores on the bottom of a microwell (3) serving as a working electrode. The reactive metal layer (1) may include through holes (4) for connection to non-reactive metal layer (5). The middle inert layer (6) includes through holes aligned with microwell (3) and through holes (4) and serves as the working distance between the metal layers. The top non-reactive metal layer (5) includes through holes aligned with microwell (3) and has an inner wall surface area in the microwell (3) that serves as the counter and/or reference electrode, and may include one or more through holes (4) that align with the microwell (3). Additional inert layers (7), serve as an effective insulation for the metal layers. One or more holes can be added and aligned with the one or more holes of any of the layers. Additional through holes (8) may be applied for connection to reactive metal layer (1). One or more holes can be added and aligned with the one or more holes of any of the layers. In some non-limiting examples, the metal layer (1) can be a non-reactive metal and the non-reactive metal layer (5) can be the reactive metal.

Figure 2:
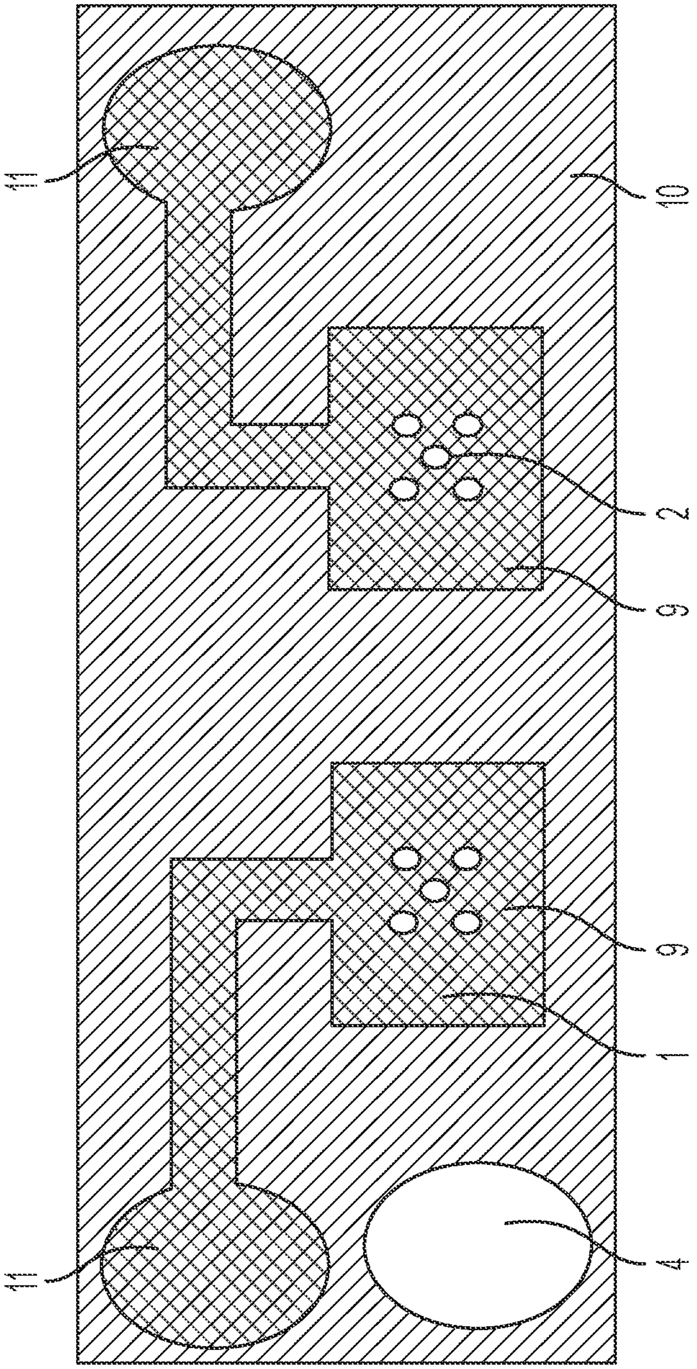
FIG. 2 shows a non-limiting embodiment in a top-sectional view of the microwell microelectrode filtration sensor.

FIG. 2 is a top schematic views of the microwell micro-electrode filtration sensor according to a non-limiting embodiment or example of the invention. FIG. 2 illustrates the construction of patterned reactive metal (9) coated onto an inert material (10) that serves the reactive metal layer (1) and working electrode surfaces. The reactive metal layer (1) may include one or more filtration membrane (2) with pores to be aligned with the microwell (3). Each patterned reactive metal area (9) may be patterned with connected pads (11) making electrical contacts to each working electrode surfaces (9). The connected pads (11) may be aligned with through holes (8) for connection to the patterned reactive metal (9) to allow electrochemical signals to be measured. The inert layers (6, 7) may contain one or more holes that align with one or more through holes (8). In some non-limiting examples, the patterned reactive metal (9) can be a non-reactive metal.

For purposes of the description hereinafter, the analyte detection microwell fabricated herein can be electrochemical detection of target analytes in accordance with the IBRI PCT. The target analytes may include a wide range of target molecules and target cells. In addition, the target analytes may be reacted with an affinity agent attached to an enzyme as a catalyst, namely alkaline phosphatase (ALP) or horseradish peroxidase (HRP), capable of generating an electrochemical signal. Other non-limiting examples of catalyst may include other enzymes, proteases, metal chelates, and organic molecules capable of producing labels capable of being oxidized or reduced. The affinity agent can be electrochemical immunoassay (EC-IA) as described (Pugia Anal Chem, 2021). This EC-IA generates an electrochemical signal as current in μA plotted against the voltage (V) across a work electrode surface with affinity agent and a counter/reference electrode surface. In another example, polyclonal affinity reagents were used as a sandwich assay pair by placing an affinity label (biotin) on some of the polyclonal antibodies and placing a detection method (Nanoparticle) on the remaining polyclonal antibodies and the EC-IA is measured by electrochemical impedance measurements (Pugia papers 1-3).

For purposes of the description hereinafter, affinity agents with electrochemical catalyst may include the chemicals needed to perform the analysis for the capture of cells and biomolecules, and generation of electrochemical signal. Affinity agents are binding agents that are specific for a cell or biomolecule. The phrase "binding partner" refers to a molecule that is a member of a specific binding pair. A member of a specific binding pair is one of two different molecules which specifically binds to a cell or biomolecule. The members of the specific binding agents may be members of an immunological reagents such as antigen-antibody or hapten-antibody, or other biochemicals such as biotin-avidin, hormones-hormone receptors, enzyme-substrate, aptamers, nucleic acid duplexes, IgG-protein A, and polynucleotide pairs such as DNA-DNA, RNA-RNA, DNA-RNA or oligo poly nucleotides like poly T or poly A.

Example of a Method of Making a Microwell Micro-Electrode Filtration Sensor

According to a non-limiting embodiment or example of the invention, microwell microelectrode filtration sensors were produced with 10 analyte detection microwells were produced by three different processes by attaching layers of planar surfaces that are aligned as shown in FIG. 1. In process 1, ceramic laser drilling with gold sputtering was use to prepare the reactive metal surface which was laminated to inert plastics which were made by machining and to copper layer as an inert metals which was processed by drilling In process 2, flexible circuit machining process was used to drill and adhere layers, with ENIG was use to prepare the reactive metal surface which was laminated to inert plastics which were made by molding. In process 2, a printed circuit machining process was used to drill and adhere layers, with ENIG was use to prepare the reactive metal surface which was laminated to inert plastics which were made by molding. In all cases, each microwell was 1.8 to 2.1 mm in diameter and ~3000 um in height and 10 microwells were demonstrated (See Table).

| Element in FIG. 1 | | Case 1 | Case 2 | Case 3 |
|---|---|---|---|---|
| 3 | Number of microwells | 10 | 10 | 10 |
| 3 | Microwell diameter (mm) | 2.1 | 1.8 | 1.8 |
| 3 | Microwell height (mm) | 3 | 3 | 3 |
| 3 | Microwell volume (uL) | 9.4 | 7.7 | 7.7 |
| 7 | Inert material | Teflon | COP/PI | COP/FR4 |
| 5 | RE/CE material | Copper | Copper | Copper |
| 5 | RE/CE distance (microns) | 100 | 70 | 70 |
| 5 | RE/CE surface area (mm^2 per microwell) | 0.56834 | 0.4 | 0.4 |
| 6 | Working distance (microns) | 200 | 210 | 130 |
| 6 | working distance surface area (mm^2 per microwell) | 1.25 | 0.79 | 0.8 |
| 6 | Working distance material | Teflon | PI | FR4 |
| 1 | WE material | Aluminia | Copper/PI/ Copper | Copper |
| 1 | WE material thickness (microns) | 50 | 12 | 12 |
| 1 | WE coating | Sputtered Gold | ENIG | ENIG |
| 1 | WE surface area in microwell (mm^2 per microwell) | 3.1 | 3.1 | 2.54 |

-continued

| Element in FIG. 1 | | Case 1 | Case 2 | Case 3 |
|---|---|---|---|---|
| 2 | Pore diameter (microns) | 100 | 100 | 200 |
| 2 | Pore number | 8 | 10 | 4 |
| 2 | Porosity (mm^2 per microwell) | 0.0628 | 0.081 | 0.128 |
| 7 | Bottom material | Teflon | FR4 | FR4 |
| 7 | Bottom protector thickness (microns) | 300 | 300 | 300 |

The bottom reactive metal layer was comprised of gold with an area of 3.1 to 2.5 mm^2 per microwell and the microwell volume of 9.4 to 7.7 uL. The reactive metal layer covers the bottom of the microwell. The reactive metal area had 10 to 4 pores of 100 to 200 um diameter for a porosity of 0.063 to 0.128 mm^2 per microwell. A non-reactive metal layer of 100 mm thick copper served as the counter and/or reference electrode area with a surface area 0.63 mm^2 per microwell. An inert layer 6 served non-reactive layer has an effective working distance area of 1.25 to 0.8 mm^2, which about half the size of working electrode area of 2.5 mm^2.

Materials:

| | |
|---|---|
| Microwell micro-electrode filtration sensor (FIG. 1) | Sensors were produced by the processes and dimension shown above which included a size exclusion filter, electrochemical detector, and allowed attachment of affinity agents for a target analyte for capture and detection by method described below. Sensors were fabricated under contract by Vishay (Shelton, CT). |
| Sensor holder | The reagent and filtration wells were produced by CNS mill of PEEK by fictiv (San Francisco, CA) or molded in COP by Makuta Technics Inc (Shelbyville, IN) according to design CAD produced by Edmonds Engineering (San Francisco, CA) as 10004 BioMEMS REAGENT WELL REV 05, and 10005 BioMEMS FILTRATION WELL REV 05 which represents the top and bottom of sensor holder (22) in FIG. 4 and variations thereof. A capillary of 0.3 mm diameter and 2.0 mm length was placed the bottom filtration well as capillary stop. The reagent well has a diameter of 9.5 mm and height of 14.5 mm for a usable volume of 1.1 mL. |
| Electrochemical calibrators | Biotinylated enzyme (ALP-biotin,) with alkaline phosphatase (ALP) as catalyst, biotinylated enzyme (HRP-biotin) with horse radish peroxidase (HRP) as catalyst, and biotinylated gold nanoparticle (NP) of 5 to 100 nm diameter as catalyst, (Sigma Aldrich) were uses a examples of as electrochemical catalyst |
| Electrochemical solutions | The ALP signal generating reagent used an electrochemical solution of 1.05 mM solution of p-amino-phenyl phosphate (pAPP, 3.0 mg, MW 189) in 100 mM TRIS, 600 mM NaCl, and 5 μM MgCl2 adjusted to pH 9.0. The NP signal generating reagent used an electrochemical solution of 5 mM potassium ferricyanide, 5 mM potassium ferrocyanide, 100 mM Tris-HCl pH 8, and 0.2% Tween-20. |
| Capture antibodies | Polyclonal antibodies recognizing *S. aureus* (Thermo Fisher Scientific), *E. coli* (MyBioSource, San Diego, CA, USA), *K. pneumoniae* (Thermo Fisher Scientific) and *P. aeruginosa* (Abcam, Cambridge, UK) conjugated to biotin-PEG4 using EZ-Link NHS-conjugation kits (Thermo Fisher Scientific). The resultant antibody conjugates were stored at 4° C. |
| Detection antibodies | Detection antibodies were polyclonal antibodies recognizing *S. aureus* (Thermo Fisher Scientific), *E. coli* (MyBioSource, San Diego, CA, USA), *K. pneumoniae* (Thermo Fisher Scientific) and *P. aeruginosa* (Abcam, Cambridge, UK) separately conjugated to alkaline phosphatase (ALP) or horse radish peroxidase (HRP) as catalyst (Thermo Fisher Scientific) or to gold nanoparticle (NP) of 5 to 100 nm diameter as catalyst (Sigma Aldrich). The resultant antibody conjugates were stored at 4° C. |

Unless otherwise noted, all other materials were purchased from Sigma Aldrich or Thermo Fisher Scientific.

Example of a Method of Making a High Affinity Capture Surface

Affinity agent for capture was attached to the reactive metal in the microwell using the following non-limiting procedure. The neutravidin is linked to the gold surface by modification of the working electrode to functionalize the surface with a linkage arm (15) with neutravidin. This is performed by the 11-MUA, EDC and HHSS method. This fabrication starts with dissolving 1.0 mM of 11-Mercapotundecanoic acid (11-MUA) into 50 mM phosphate buffer solution at pH 10. Next, 1 μL of the solution is added to each microwell of the sensor and allow to sit overnight. The sensor was washed with water 5 times and heated at 37 C until dry. The terminal carboxylic groups (of 11-MUA) were then activated for 1 h by applying 1 μL of 75 mM N-(3-dimethylaminopropyl)-N-ethylcarbodiimide hydrochloride (EDC) and 15 mM (N-hydroxy-succinimide ester (NHSS) in 50 mM phosphate buffer solution at pH 6.1. The plate was washed with water 5 times and heated at 37 C until dry. Next, only the surface of the working electrode is treated with 5 μL of neutravidin (Thermo fisher Prod. 31000) dissolved at 1.0 mg/mL into 50 mM phosphate buffer and reacted for 30 min to immobilize at 37 degrees C. until dry. The plate was washed with water 5 times and heated at 37 C until dry. In other non-limiting examples, the neutravidin was replaced with alkaline phosphatase (1.7 mg/ml) and the electrochemical reporter was directly linked to microwell.

After functionalization, micro-filtration sensors were blocked with 200 μL solution of blocking buffer. The blocking buffer was made with 112.5 mL of water containing 10% Candor (Candor Bioscience, Cat. #110125), 3.18 g MOPSO, 1.50 g BSA (Bovine Serum Albumin (Fraction V), and 60 uL Proclin 200 and pH was adjusted to 7.5 with 10 N sodium hydroxide and the buffer. After blocking overnight the micro-filtration sensors were washed five times with 200 μL of TBS-T (Tris buffered saline with 0.05% Tween-20) and allowed to air dry.

Additionally, there are additional non-obvious benefits of the reactive metal with gold surfaces in the device, such as providing reduced expense as opposed to carbon. It is possible for only an ultra-thin monolayer to actively functionalize 11-mercaptoundecannoic (11-MUA) acid to form a self-assembled monolayer and to allow a reaction with affinity capture agents using 1-ethyl-3-(-3-dimethylaminopropyl) carbodimide (EDC) and N-hydroxysulfosuccinimide (NHSS) onto the working electrode at the bottom of the microwells. Additionally, gold can be deactivated with 11-mercaptoundecannoic (11-MUA) acid in the absence of EDC treatment. Therefore, a reactive metal for a WE can be converted to a non-reactive metal for a CE/RE where conductive properties are matched. Silver/silver chloride also can be used because it is less costly than gold; however, it is less reactive. An additional benefit was that the device could be rapidly assembled by automated alignment of holes after drilling and milling by adhesion of sheets of materials for each layer. The device also allowed ease of functionalization as the microwells can be used to hold the treatment liquids and can be washed using vacuum filtration during the manufacturing processes. This allows a simple automated dispensing station to automate the process.

In some non-limiting embodiments or examples, several different types of high affinity capture agents (e.g. neutravidin, anti-FITC, anti-Digitoxin, etc.) are functionalized to allow capture of tagged affinity agents (e.g., Biotin, FITC, Digitoxin: etc.). Unique high-affinity agent surfaces are used in each microelectrode to allow multiplexed results. The antibody reagents used for different antigens are kept separated in different microwells.

Example of Methods to Process Sample and Perform EC-IA Analysis:

These sensors did allow biomolecule and calibrators to be captured from complex samples under low hydrodynamic force and detection biomolecule by detection of electrochemical labels. The electrochemical label or redox probes were detected by the reactive metal surface layer as the working electrode and the non-reactive metal surface layer as the reference electrode and/or counter electrode (as described below).

Figure 3:
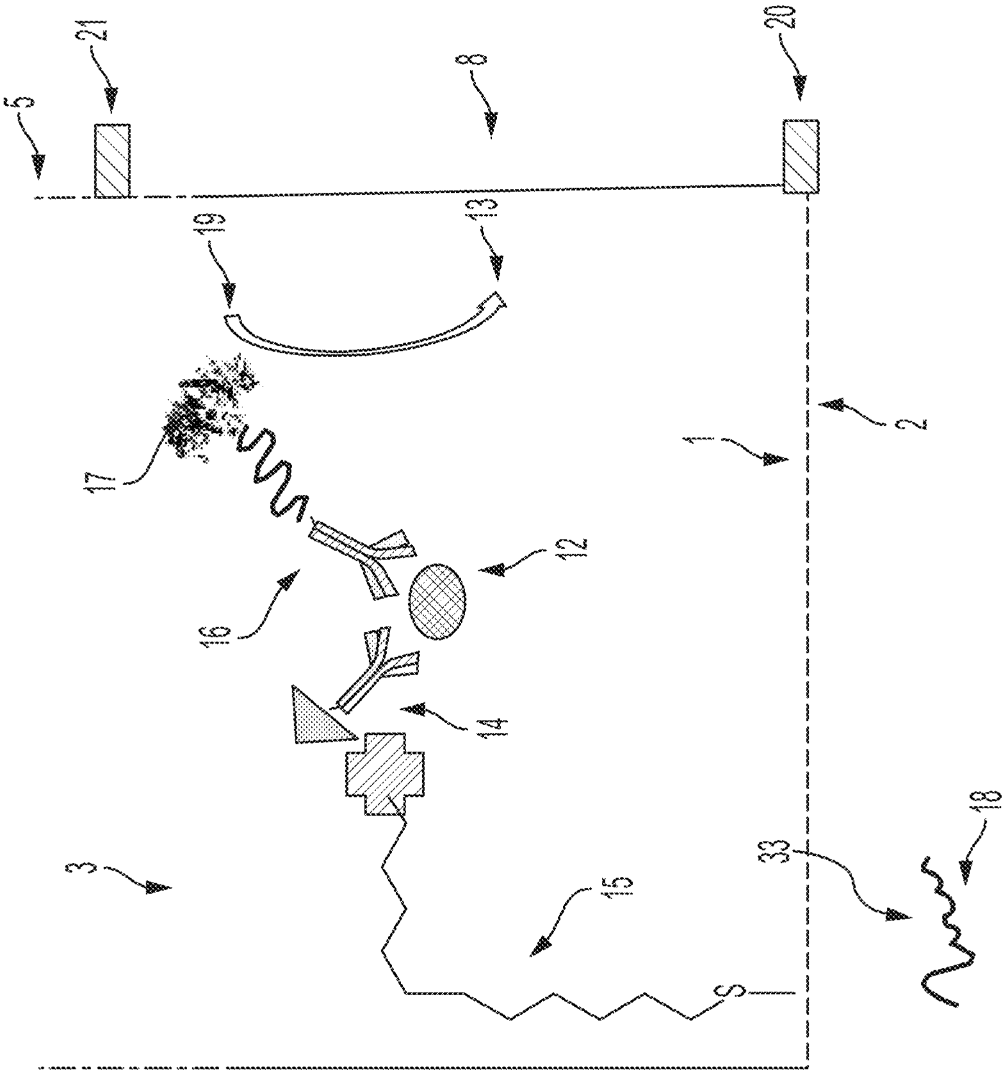
FIG. 3 shows a non-limiting embodiment in a schematic view of the electrochemical analysis of a sample.
Figure 4:
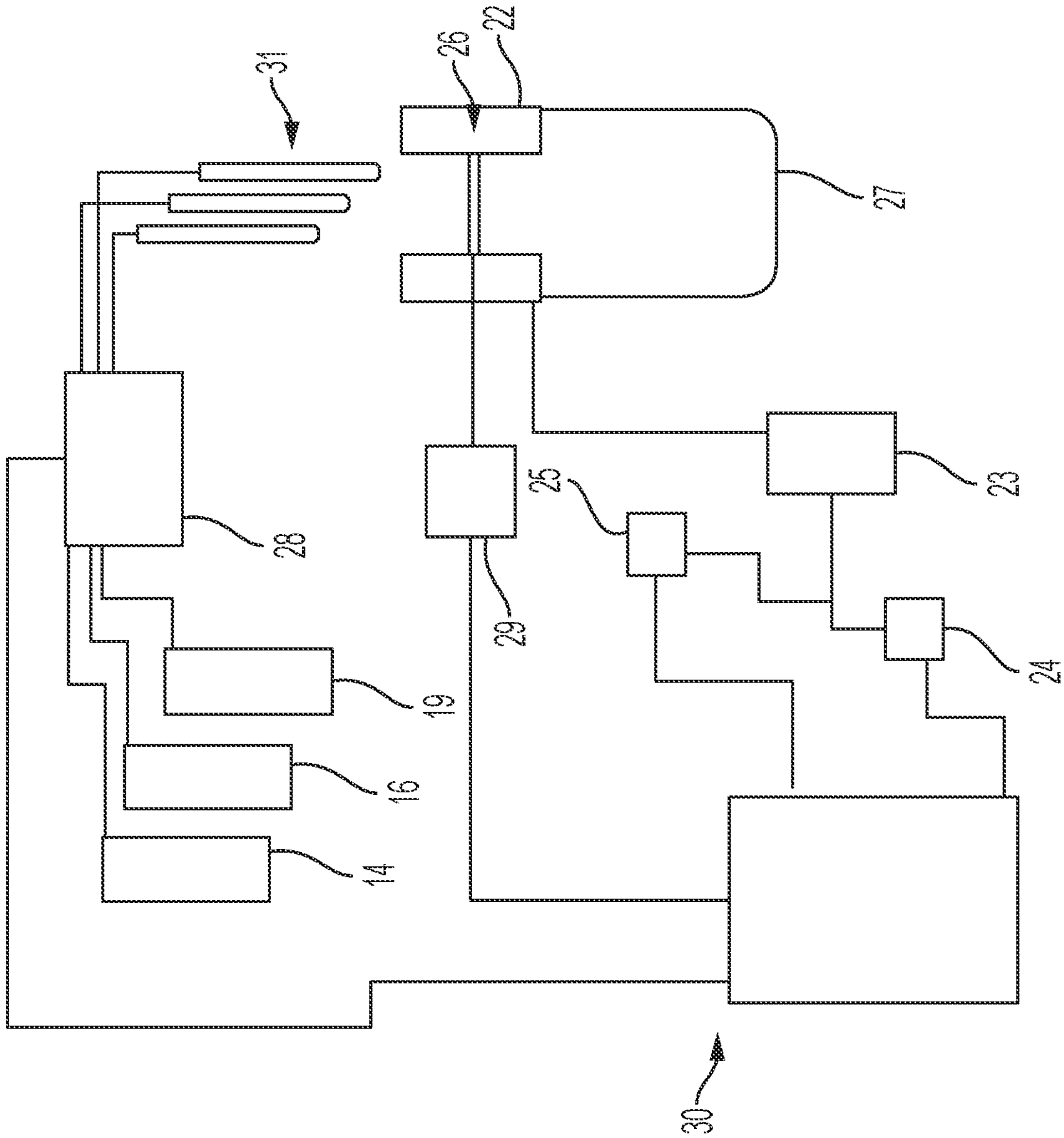
FIG. 4 shows a non-limiting embodiment of a system for analyte detection and analysis in a schematic view.
Figure 5:
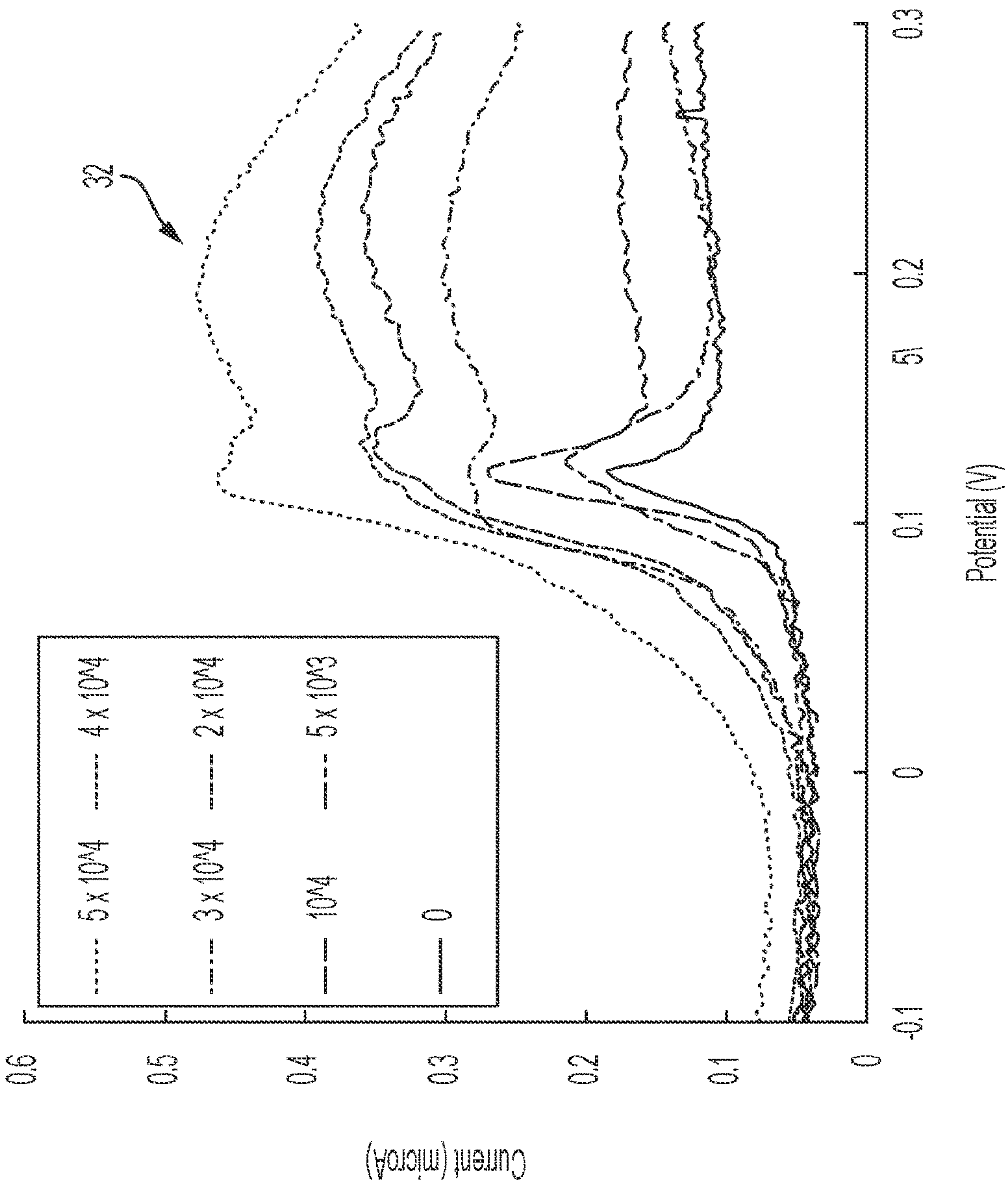
FIG. 5 shows the electrochemical response after addition of sample in accordance with the disclosure of the invention.

These sensors were able to processed by the system shown in FIG. 4 with EC-IA reagents (14, 16, and 19) with catalyst (17) as shown in FIG. 3. In some examples, alkaline phosphatase can be the catalyst (17) and is used to generate para-amino phenol as the generated electrochemical signal (13) from para-amino-phenyl phosphate (19) to produce results like those as shown in FIG. 5. In another methods, horse radish peroxidase (HRP) can be used the catalyst to generate quinonimine as the generated electrochemical signal (13) from para-amino-phenyl phenol (19) with hydrogen peroxide. In another method, gold nanoparticle (NP) can be used as the catalyst to generate a change in impedance as the generated electrochemical signal (13) using ferrous cyanides (19) as the redox probe in the electrochemical solutions to generated electrochemical signal (13).

FIG. 4 illustrates a non-limiting embodiment or example in a schematic view of the system used in the example, with vacuum pump (23) connected to vacuum pump motor driver (24) and pressure sensor (25) as the hydrodynamic force for capturing cells and biomolecules from a sample on a micro-filtration sensor with microwell (3) and size exclusion filtration membrane (2) for the filtration of the sample. The micro-filtration sensor (26) is sealed to a waste containment area (27) using a sensor holder (22) for the micro-filtration sensor (26). The system uses a vacuum filtration driven by an Arduino based proportional-integral-derivative (PID) controller logic to maintain the desired pressure in the waste containment area (27). A shown by directional arrow (33) in FIG. 3, the vacuum also drives the sample and liquid reagent fluids through the filtration membrane (2) in microwell (3) held in a plastic format as a sensor holder (22). The system may also serve as a sample processor by using vacuum as the hydrodynamic force for capturing cells and/or biomolecules and analysis reagents on to the functionalized size exclusion filtration membranes (2) in the microwell (3) of the micro-filtration sensor (26), as shown in FIG. 1. Negative pressure for filtration was provided by vacuum via underside of the filtration membrane (2).

The system shown in FIG. 4, may also include fluidic dispensers for addition of liquid reagents (14, 16, 19) by programmable dispensing pumps (28) and a potentiostat (29) as electronics for detection of electrochemical signals in the micro-filtration sensor (26). An Arduino programmable controller board (30) with a menu-driven program (Adafruit Industries, New York, NY, USA) was used to control the programmable dispensing pumps (28), vacuum pump motor driver (24) and potentiostat (29) as well as to power, monitor, and regulate vacuum pressure for filtration (at 10-100 mbar negative pressure±10%). An MPXV5050DP analog differential pressure sensor (25) (Mouser Electronics, Mansfield, TX, USA) was used to measure the pressure in a conical 50-mL Falcon tube or 5-ml Eppendorf tube to serve as the waste containment area (27). Arduino-based vacuum-driven fluidic control system including proportional-integral-derivative (PID) control to maintain a user-defined pressure in the containment area (27). The control loop also drives a DC diaphragm pump (23) (22000.011, Boxer Pumps, Ottobeuren, Germany) through a DRV8838 brushed DC motor driver (Texas Instruments, Dallas, TX, USA) was to evacuate air from the containment area (27). The vacuum pump (23) and the pressure sensor (25) were connected to a conical tube using appropriate fluidic connectors (IDEX Health & Science, Oak Harbor, WA, USA). The liquid dispensing was controlled using the same Arduino programmable controller board (30) using three peristaltic pumps with linear actuator motors as the programmable dispensing pumps (28) to pump liquids (14, 16 and 19) into microfiltration sensor (26) using sample delivery (100 uL±1%) through liquid dispensing needles (31).

EC-IA analysis can be conducted on these sensors according to FIG. 3 used biotinylated capture of antibody (14), and detection antibody (16) labeled with alkaline phosphate (ALP) as catalyst (17) and electrochemical signal generating reagent (pAPP) (19) as described (Pugia Anal Chem 2021). In another examples detection antibody (16) is replaced with electrochemical calibrators with biotin and the catalyst (17) and serves to measure response in the absence of analyte, capture of antibody (14), and detection antibody (16). Neutravidin was linked to the reactive metal layer (1), which in this case gold, as the working electrode (21) surfaces through the linkage arm (15) as described above. Also pictured in FIG. 3 are the reference electrode (20) and non-target complexes (18) such as non-target analytes.

In another examples, demonstration, capture and detection specific for *P. aeruginosa* bacterial analyte can be used as shown in literature. Bacterial lysates are prepared at 5×10^3 to 5×10^4 cell/mL prepared by addition of BPEP-II surfactant (Pugia Anal Chem 2021). Antibody reagents are added manually to buffer the complex sample with analyte (12) and incubated at 37 C to make the antibody complex for capture. A sample contained 100 μL of the lysate sample (0, 5, 10, 20, 30, and 40 thousand cells or lysate equivalent per assay) were added to the 48 μL of the biotinylated *S. aureus, E. coli*, or *P. aeruginosa* polyclonal antibodies (0.75 μg/assay), and incubated for 1 h at room temperature.

In this non-limiting EC-IA analysis method, the liquids were moved by the analyzer by using the program control logic controller (PID): Step 1) was drawing a complex sample with antibodies down into micro-wells through turning the vacuum; Step 2) was keeping the complex sample with antibodies in the microwells for incubation through turning the vacuum off; Step 3) was the incubation of antigen and the antibodies complex in sensor microwells for 5 minutes allowing the antigen affinity complex to be captured by the neutravidin attached to size exclusion filtration membrane through a linkage arm; Step 4) the addition and removal of wash solutions five times as 200 μL of TBS-T (Tris buffered saline with 0.05% Tween-20) to allow removal of unbound materials. The analyzer accomplished these steps using the peristaltic pump with linear actuator motors to dispense the TBS-T, wash and then vacuum to remove the TBS-T wash from the size exclusion filtration membrane.

Testing demonstrated that the complex sample and liquid reagents flow through the microwell microelectrode filtration sensor attached to a reaction well, and then into waste without any need to change the hydrodynamic pressures. Additionally, there was no clogging due to debris from complex samples. Removing the vacuum allows the sample and liquid to be held in the reaction well and the filtration well.

The potentiostat circuit board allowed measurements that would be needed for the EC-IA analysis from 3 μA to 50 nA current across working and reference/counter microelectrodes for −0.1 to 0.3 V. FIG. 5 shows the electrochemical signal generated (32) as current in μA plotted against the voltage (V) for and immunoassay detection (EC-IA) based on ALP as an catalyst and having the antibodies directly on the to the binding surface for samples including 0, 5, 10, 20, 30, 40 or 50 thousand lysate equivalent of bacterial cells per assay. The immunoassay detection (EC-IA) directly on the binding surface achieved a quantitative bacterial immunoassay enumeration of cell counts across a range of 5,000 to 40,000 bacteria per sample increasing concentration of analyte. For example, 333 and 33 pM of ALP would be expected to produce average current change of 2.4 and 0.8 μA at 0.2 V in 5 min using an electrochemical reaction solution with 1 mM pAPP, 100 mM TRIS (3.1 g/200 mL), 600 mM NaCl (7.0 g/200 mL), & 5 M MgCl (0.2 g/200 mL) adjusted to pH 9.0. The ALP activity is optimal in basic pH range of 8 to 9, falls rapidly to little reactivity at pH 6.3.

In practice, several other different types of catalyst (17) are possible for electrochemical immunoassay (EC-IA) such as other enzymes such as beta-galactosidases, oxidases, dehydrogenases, catalases, and reductases to name a few (Nguyen 2019). In other examples other several different types of nanomaterials were possible as catalyst (17) such oxide nanoparticles, metal nano particles, nano spheres, nano-rods with various redox probes as the signal generating reagent (Luo 2005, Zhu 2015). In practice, several different electrochemical methods can be used to detect the signal amperometry, potentiometry, conductometry, and impedimetric methods such as impedance spectroscopy (EIS) (Nguyen 2019, Pugia Anal Chem 2021, Pugia papers 1-3 for NP)

Testing demonstrated that the electrochemical signals were detected by all these sensors, using application of a reference voltage and detecting the signal generated using working/counter electrodes by a change in current measured across a working distance with the counter electrode. The analyzer used the potentiostat which was able to read and control the sensor microwells voltage. The potentiostat circuit board used for these measurement of 100 μA to 50 nA current across working and reference/counter microelectrodes for −0.1 to 1.0 V and showed these sensor worked all the typical modes used for electrochemical detection tested.

The separation of the surface areas of the working (WE), reference (RE), and counter electrodes (CE) were acceptable and the redox probes was detected in all cases. Ideally the surface area of the combined counter/reference electrode (CE/RE) should have been maximized and at least the surface area of the working electrode (WE). Ideally the separation or effective working distance, between WE and RE/CE, should be optimized for improving the response of the electrode and is typically smaller working distances. Surprisingly, we found CE/RE area of 0.63 mm^2, almost a quarter WE area of 2.5 mm^2 sufficed. Additionally, the large working distance area of 1.25 to 0.8 mm^2 and larger working distance gap of 130 to 200 μm still allowed detection from the WE without having to work with smaller working distance gap. The addition of separate CE and RE and multiples layers of CE and RE are only expected to improve the sensitivity and the surface increases.

In this embodiment or example, the number of WE array could be detected with 10 patterned or more connections, and 1 connection for a common counter and reference electrode (CE/RE electrode). This 2-electrode system allowed the CE/RE to be shorted together. The traditional separation of the RE and CE electrodes are only needed in case of high interference with the Cl which is not a concern for affinity binding reactions. In example, the 2-electrode design with a common CE/RE electrode that could be read in a timing cycle against each WE for each microwell can be used. An additional benefit occurs since the electrochemical signal is only measured across the WE and CE/RE having liquids areas in the sensor above or below this space have less of an impact. This allows a much greater tolerance for how fast the hydrodynamic pressure is adjusted and how accurately the flow of liquids is stopped and as long as enough of a sample is presented between the used samples. An additional benefit occurs since the electrochemical signal is only measured across the WE and CE/RE.

While the invention has been illustrated and described in detail in the drawings and foregoing description, the same is to be considered as illustrative and not restrictive in character, it being understood that only the representative embodiments have been shown and described and that all changes, equivalents, and modifications that come within the spirit of the invention defined by the claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A microwell microelectrode filtration sensor, comprising:

a microwell, the microwell comprising:

a reactive metal layer with a diameter greater than 100 μm comprising one or more pores with a diameter greater than 10 μm, and wherein the reactive metal layer has a portion of a top planar surface and a portion of a bottom planar surface exposed inside the one or more pores;

at least one inert layer;

at least one non-reactive metal layer, wherein the at least one inert layer is placed between the reactive metal layer and the at least one non-reactive metal layer; and an affinity capture agent disposed on said portions of the top and bottom planar surfaces of the reactive metal layer.

2. The microwell microelectrode filtration sensor of claim 1, wherein the at least one inert layer comprises an effective working thickness of greater than 50 μm.

3. The microwell microelectrode filtration sensor of claim 1, wherein the at least one non-reactive metal layer comprises an effective inner microwell surface area smaller than a working electrode surface area.

4. The microwell microelectrode filtration sensor of claim 1, wherein the reactive metal layer comprises copper or gold.

5. The microwell microelectrode filtration sensor of claim 1, wherein the affinity capture agent is neutravidin, anti-FITC, or anti-Digitoxin.

6. The microwell microelectrode filtration sensor of claim 1, further comprising a second inert layer covering at least a portion of the at least one non-reactive metal layer.

7. The microwell microelectrode filtration sensor of claim 1, further comprising a third inert layer, wherein the third inert layer is in contact with at least a portion of the reactive metal layer.

8. The microwell microelectrode filtration sensor of claim 1, further comprising at least one pad, wherein the at least one pad is in electrical communication with the reactive metal layer, thereby allowing measurements of electrochemical signals at the at least one pad.

* * * * *